US00PP10449P

United States Patent [19]

Zary

[11] Patent Number: Plant 10,449

[45] Date of Patent: Jun. 16, 1998

[54] FLORIBUNDA ROSE PLANT NAMED 'JACEVE'

[75] Inventor: Keith W. Zary, Thousand Oaks, Calif.

[73] Assignee: Bear Creek Gardens, Inc., Medford, Oreg.

[21] Appl. No.: 800,643

[22] Filed: Feb. 14, 1997

[51] Int. Cl.[6] ..... A01H 5/00

[52] U.S. Cl. ..... Plt./26

[58] Field of Search ..... Plt./26

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class, having very long stems; very good flower production in attractive clusters; long vase life; and attractive, pure light pink flower color.

1 Drawing Sheet

The present invention relates to a new and distinct variety of rose plant of the floribunda class which was originated by me by crossing an unnamed pink floribunda seedling, with the variety INTERlien, U.S. Plant Pat. No. 7,368.

The primary objective of this breeding was to produce a new rose variety having the high centered, light pink flowers presented in clusters on long stems of the female parent combined with the well-formed sprays, long vase life, and vigorous upright growth habit of the male parent. The objective was substantially achieved, along with other desirable improvements, as evidenced by the following unique combination of characteristics that are outstanding in the new variety and that distinguish it from its parents, as well as from all other varieties of which I am aware:

1. Very long stems;
2. Very good flower production in attractive clusters;
3. Long vase life;
4. Attractive, pure light pink flower color.

Asexual reproduction of theis new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed floribunda.

*Pollen parent.*—INTERlien (U.S. Plant Pat. No. 7,368).

Classification:

*Botanical.*—*Rosa hybrida.*

*Commerical.*—Floribunda.

FLOWER

Observations made from specimens grown in a greenhouse environment at Somis, Calif. from March 1996 to January 1997.

Blooming Habit: Recurrent.

Bud:

*Size.*—1 to 1¼ inches long when the petals start to unfurl.

*Form.*—The bud form is long, pointed ovid.

*Color.*—When sepals first divide, bud color is Red Group 49D. When half blown, the upper sides of the petals are Red Group 49D; and the lower sides of the petals are Red Group 49D.

*Sepals.*—Color: Green Group 138B. Surface texture: Covered in fine hairs. There are three lightly appendaged sepals. There are usually two unappendaged sepals with hairy edges, but occasionally there is a third unappendaged sepal.

*Receptacle.*—Color: Green Group 137C. Shape: Funnel. Size: Small (⅛×5/16 inch). Surface: Smooth.

*Peduncle.*—Length: Short (1 inch to 1½ inches). Surface: Glandular (many small glands). Color: Medium green. Strength: Stiff, erect.

Bloom:

*Size.*—Small. Average open size is 1½ to 1¾ inches.

*Borne.*—Several together, in clusters (5 to 7 flowers). If in clusters: Pyramidal.

*Stems.*—Very long, strong. Average length is about 22–26 inches.

*Form.*—When first open: High centered. Permanence: Retains its form to the end; outer petals curl back; quill fashion.

*Petalage.*—Number of petals under normal conditions: 35–40.

*Color.*—The upper sides of the petals are Red Group 49D. The reverse sides of the petals are Red Group 49D. The base of each petal has a very small (1/64×1/64 inch) greenish white dot at the point of its attachment. The major color on the upper side is Red Group 49D.

*Variegations.*—Guard petals have greenish white midribs.

*Discoloration.*—The general tonality at the end of the first day: No change. At the end of the third day: No change. There is no color change through day seven on the plant when the petals shatter.

*Fragrance.*—Slight.

Petals:

*Texture.*—Thick.

*Shape.*—Deltoid to rounded.

*Form.*—Tips slightly recurved; edges slightly quilled.

*Arrangement.*—Imbricated, with few petaloids in the center.

*Persistence.*—Drop off cleanly.

*Lastingness.*—On the plant: Long (7 days). As a cut flower: Very long (13 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Greenish white.

*Stigmas.*—Color: Greenish white.

Form: Bush.

Growth: Very vigirous; upright; branching. At one year, without pruning, JACeve will grow 7–8 feet tall and be 3–4 feet wide. Plant will produce 170–180 stems per square meter of greenhouse.

Foliage:

*Number of leaflets on normal mid-stem leaves.* —5 or 7.

*Size.*—Small (3×2 inches).

*Quantity.*—Abundant.

*Color.*—New foliage: Greyed-red Group 178B but very quickly becoming green. Old foliage: Green Group 136A on upper surface; Green Group 136C on lower surface.

Leaflets:

*Shape.*—Pointed oval.

*Texture.*—Upper side: Glossy.

*Edge.*—Serrated.

*Serration.*—Single, small.

*Petiole rachis.*—Color: Green.

*Petiole underside.*—Smooth, with occasional prickles.

*Stipules.*—Short (⅜ inch), serrated, bearded.

*Disease resistance.*—Resistant to mildew under normal growing conditions at Somis, Calif. Not tested for rust or blackspot resistance.

Wood:

*New wood.*—Color: Green. Bark: Smooth.

*Old wood.*—Color: Green. Bark: Smooth.

Prickles:

*Quantity.*—On main canes from base: ordinary. On laterals from main canes: ordinary.

*Form.*—Short (⅜ inch), straight to hooked slightly downward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by the unique combination of its very long stems; very good flower production in attractive clusters; long vase life; and attractive, pure light pink flower color.

* * * * *

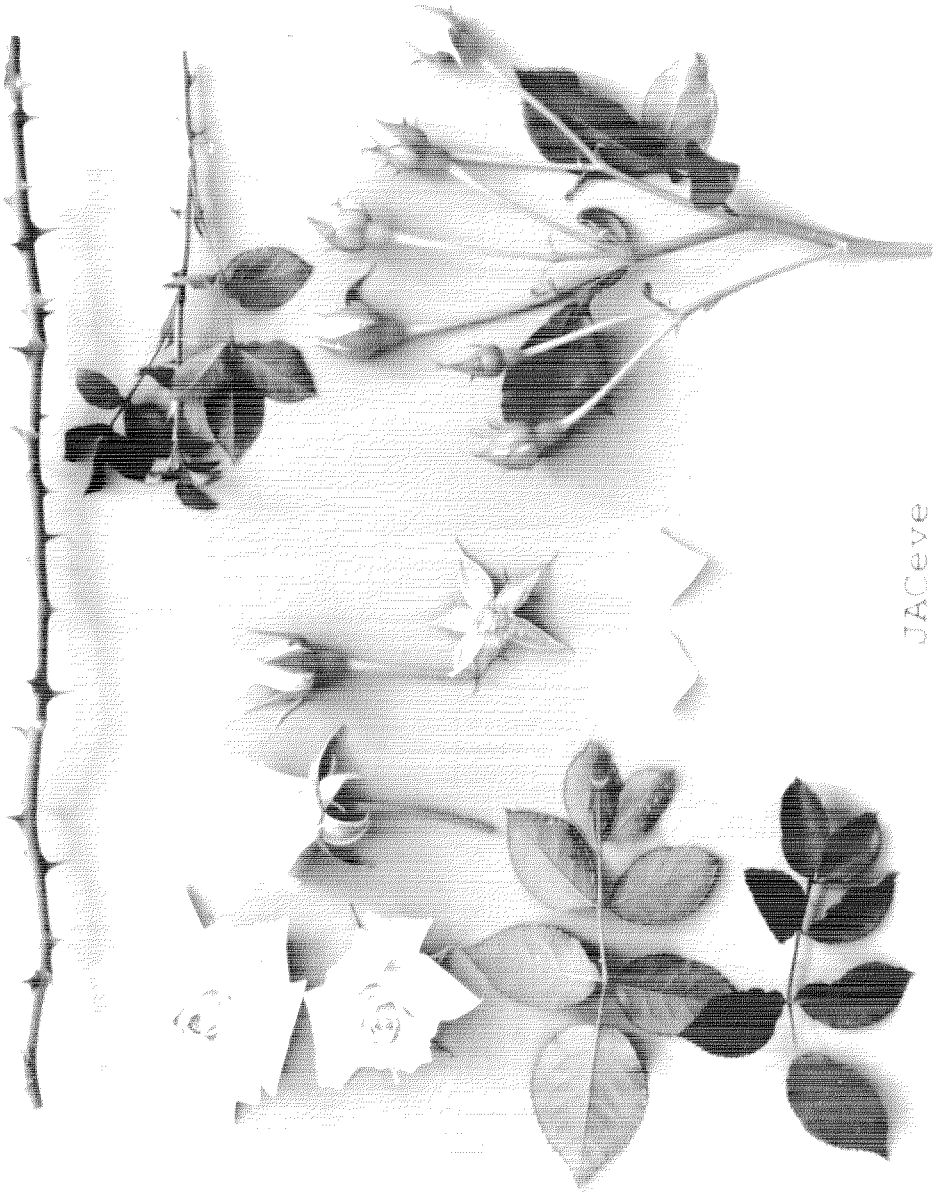
JACeve